(12) United States Patent
Lang et al.

(10) Patent No.: US 7,051,495 B2
(45) Date of Patent: May 30, 2006

(54) METHOD OF PACKAGING INTEGRATED BIOSENSORS

(75) Inventors: David K. Lang, Inverness (GB); Peter A. Rae, Inverness (GB)

(73) Assignee: Lifescan Scotland Limited, Inverness (GB)

( * ) Notice: Subject to any disclaimer, the term of this patent is extended or adjusted under 35 U.S.C. 154(b) by 0 days.

(21) Appl. No.: 10/881,560

(22) Filed: Jun. 29, 2004

(65) Prior Publication Data

US 2005/0284110 A1 Dec. 29, 2005

(51) Int. Cl.
*B65B 5/10* (2006.01)
(52) U.S. Cl. .......................... 53/475; 53/473; 53/247; 53/252; 53/185
(58) Field of Classification Search .................. 53/247, 53/252, 255, 258, 475, 158, 539, 473
See application file for complete search history.

(56) References Cited

U.S. PATENT DOCUMENTS

| | | | | |
|---|---|---|---|---|
| 5,657,610 A | * | 8/1997 | Dietrich et al. | 53/252 |
| 5,787,680 A | * | 8/1998 | Tisma et al. | 53/252 |
| 6,079,191 A | * | 6/2000 | Borkiewicz et al. | 53/252 |
| 6,202,392 B1 | * | 3/2001 | Greenwell et al. | 53/258 |
| 6,315,108 B1 | | 11/2001 | Bootsman et al. | |
| 6,804,931 B1 | * | 10/2004 | Pike | 53/252 |
| 2003/0143113 A2 | | 7/2003 | Yuzhakov et al. | |
| 2003/0211619 A1 | | 11/2003 | Olson et al. | |

FOREIGN PATENT DOCUMENTS

| | | |
|---|---|---|
| EP | 0753747 A | 1/1998 |
| EP | 1360932 A1 | 11/2003 |
| EP | 1360935 A | 11/2003 |
| GB | 672939 A | 5/1952 |
| WO | WO 01/64105 A1 | 9/2001 |
| WO | WO 02/49507 A1 | 6/2002 |
| WO | WO 03/015627 A2 | 2/2003 |

* cited by examiner

*Primary Examiner*—Louis Huynh
(74) *Attorney, Agent, or Firm*—Bernard Shay

(57) ABSTRACT

A method of loading medical devices into medical device packages utilizing an apparatus including a pusher plate, a retaining member, a transfer member and a package support member, the retaining member and the transfer member each includes a plurality of grooves for receiving and retaining the medical devices and the package support member includes a plurality of recesses for receiving and retaining the medical device packages, wherein the medical device packages are loaded into the package support member recesses, the medical devices are loaded into the retaining member grooves, every other medical devices are transferred from the retaining member to the transfer member by the pusher plate, the transfer member is urged into alignment with the package support member, the pusher plate inserts the medical devices in the transfer member into the packages in the package support member and the packages are removed from the apparatus for further processing.

1 Claim, 10 Drawing Sheets

METHOD OF PACKAGING INTEGRATED BIOSENSORS

BACKGROUND OF THE INVENTION

The present invention relates, in general, to medical devices containing an integrated lancet and sensor and, more particularly, to a process for packaging the medical devices including integrated lancets.

The determination of analyte concentration in physiological samples is of ever increasing importance to today's society. Such assays find use in a variety of application settings, including clinical laboratory testing, home testing, etc., where the results of such testing play a prominent role in the diagnosis and management of a variety of disease conditions. Analytes of interest include glucose for diabetes management, cholesterol for monitoring cardiovascular conditions, drugs for monitoring levels of therapeutic agents, and identifying illegal levels of drugs, and the like. In response to this growing importance of analyte characteristic (e.g., concentration) determination, a variety of analyte characteristic determination protocols and devices for both clinical and home testing have been developed.

In determining the concentration of an analyte in a physiological sample, a physiological sample must first be obtained. Obtaining and testing the sample often involves cumbersome and complicated procedures. Unfortunately, successful manipulation and handling of test elements, such as test strips, lancing members, meters and the like is to a great extent dependent on the visual acuity and manual dexterity of the user, which in the case of people with diabetes is subject to deterioration over the course of the disease state. In extreme cases people that have significant loss of sight and sensation, testing procedures can become significantly difficult and requires additional assistance from ancillary devices or personnel.

A typical procedure for making a glucose measurement with the use of a test strip involves multiple actions or steps. One manner of reducing the number of actions is by the use of integrated medical devices that combine multiple functions in order to minimize the handling of sensor and/or lancing components that may lead to contamination of the components and/or injury to the user. An example of such an integrated medical device that includes a test strip and lancet is described in International Application No. PCT/GB01/05634 (published as WO 02/49507 on Jun. 27, 2002; and U.S. patent application Ser. No. 10/143,399; published as 2003/0143113 A2 on Jul. 31, 2003), both of which are fully incorporated herein by reference.

Technological advancements have been made in test strip fabrication in which both sensor and lancing functions and the structures to provide such functions are provided on a single fully integrated medical device, as described in the aforementioned U.S. patent application Ser. No. 10/143,399. Integrated medical devices are typically in the form of strips. Web-based methods can be used to make such fully integrated medical devices which are singulated after fabrication prior to being collectively packaged in a cartridge, magazine, cassette or the like. Examples of web-based methods for making such medical devices are disclosed in U.S. patent application Ser. No. 10/142,409 published as 2003/0211619 A1 on Nov. 13, 2003) and European Patent Application EP 1360932 A1, both of which are fully incorporated herein by reference.

Integrated medical devices can be singly or collectively loaded into a storage container (s) or package(s) manually. However, this is difficult due to the small size of the devices, is time consuming, can possibly damage the lancing portion (e.g., micro-needle) as the device is inserted into the container, and can result in improper alignment of the device within the container. Examples of containers for integrated medical devices are described in co-pending U.S. patent application Ser. No. 10/666,154, which is fully incorporated herein by reference.

Still needed in the field, therefore, is an automated method of loading an integrated medical device into a container without damaging the micro-needle while ensuring that the device is at the proper orientation for subsequent extraction by a user.

SUMMARY OF THE INVENTION

In one embodiment the present invention is directed to a method of loading a plurality of medical devices into a plurality of medical device packages. In this embodiment of the invention, the method includes the steps of providing an apparatus including a pusher plate, a medical device retaining member, a transfer member and a package support member. In this embodiment of the invention, the device retaining member and the transfer member include a plurality of grooves for receiving and removably retaining a plurality of medical devices and the package support member includes a plurality of recesses for receiving and removably retaining the plurality of medical device packages therein. In one embodiment of the present invention, the method includes the steps of loading a plurality of packages into the package support member recesses, loading a plurality of integrated medical devices into the retaining member grooves, transferring the plurality of integrated medical devices from the retaining member to the transfer member, urging the transfer member into alignment with the package support member, inserting the plurality of integrated medical devices in the transfer member into the plurality of packages in the support member and removing the packages from the apparatus for further processing. In one embodiment of the present invention, the transferring step includes the steps of transferring every other medical device from the retaining member to the transfer member.

BRIEF DESCRIPTION OF THE DRAWINGS

A better understanding of the features and advantages of the present invention will be obtained by reference to the following detailed description that sets forth illustrative embodiments, in which the principles of the invention are utilized, and the accompanying drawings (wherein like numerals represent like elements), of which.

DETAILED DESCRIPTION OF THE INVENTION

Figure 1A:
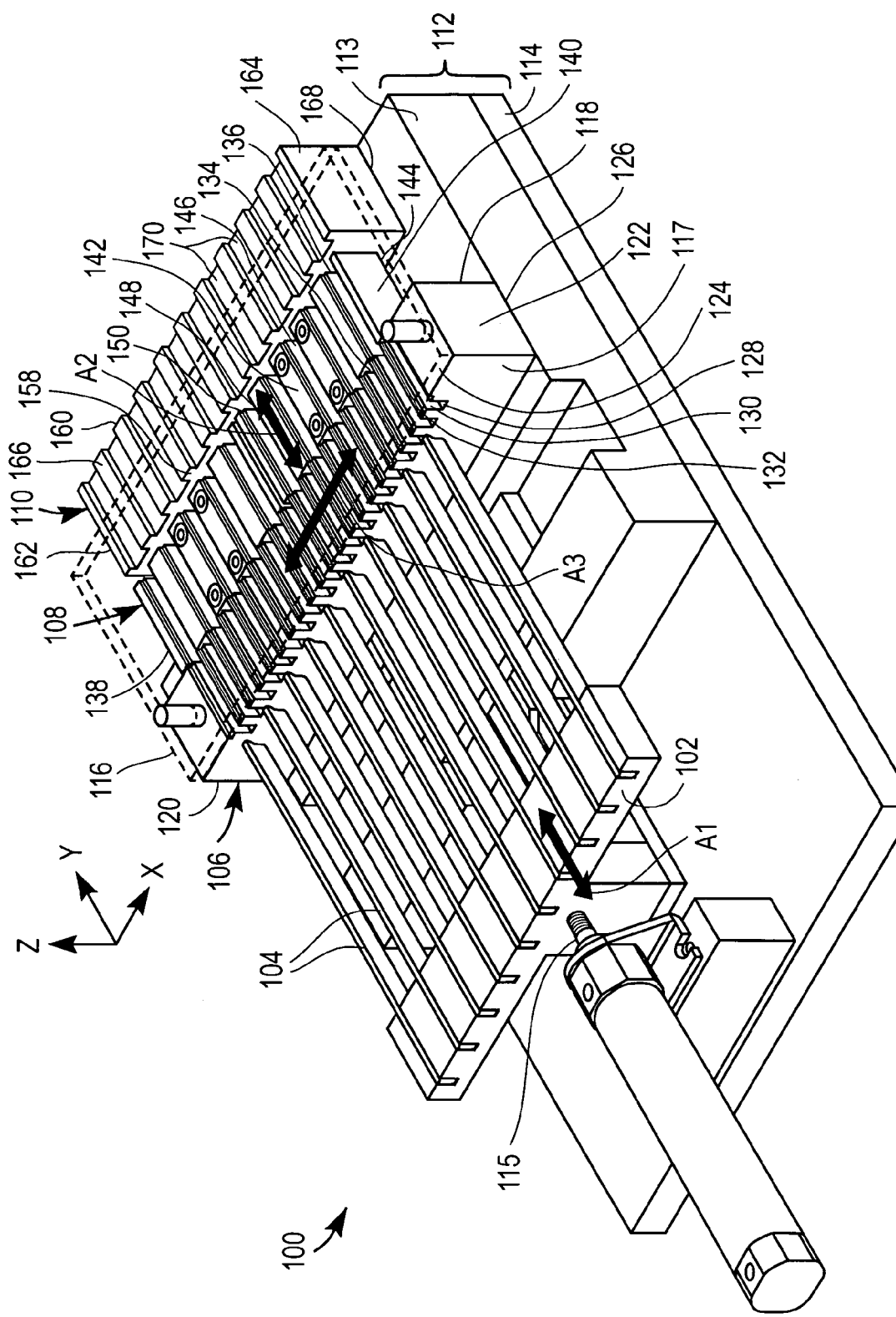
FIGS. 1A and 1B are simplified perspective and exploded perspective views of an apparatus according to an embodiment of the present invention.
Figure 1B:
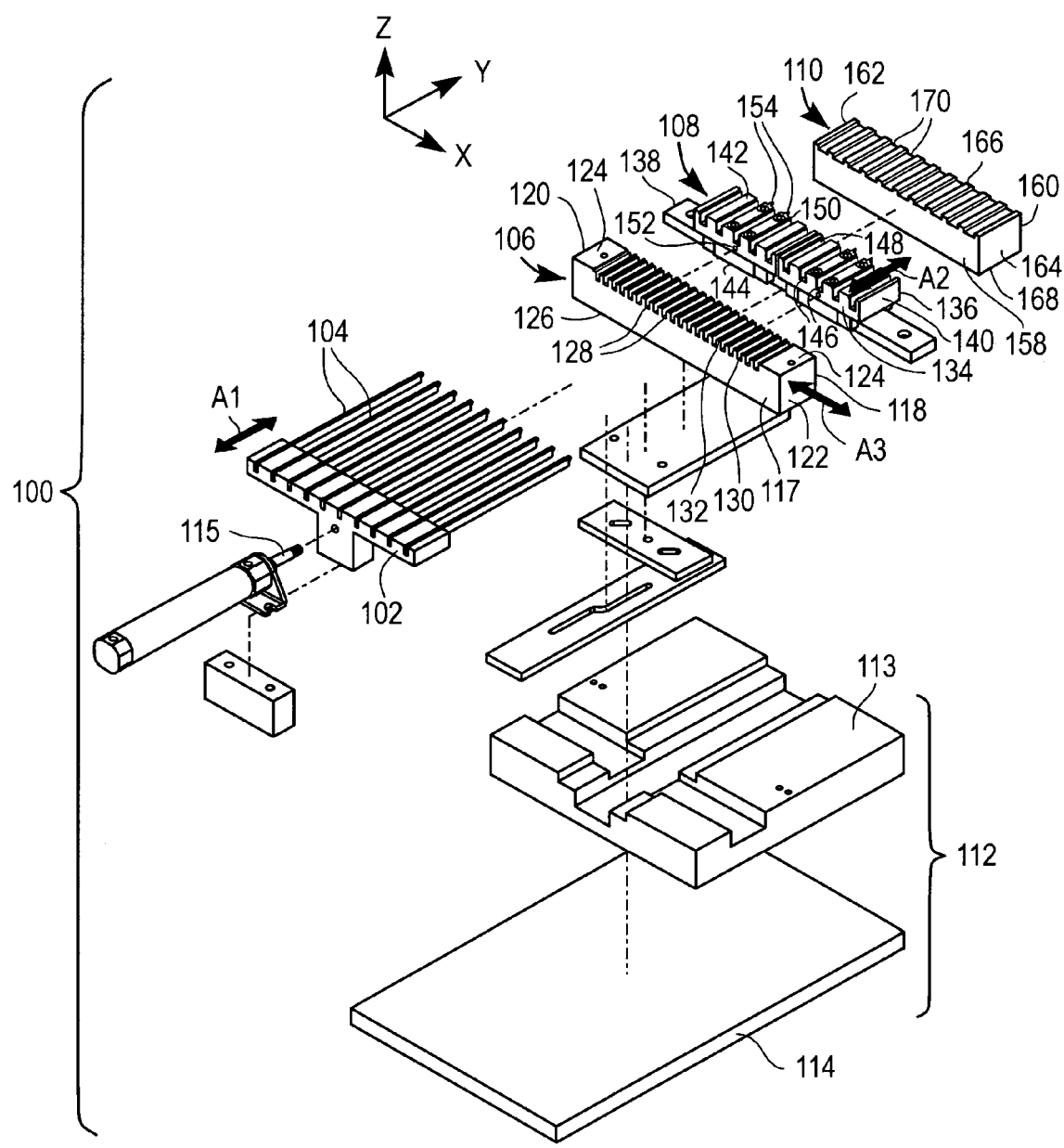

FIGS. 1A and 1B are perspective and exploded views, respectively of an apparatus 100 for loading a plurality of integrated medical devices into a plurality of medical device packages according to an exemplary embodiment of the present invention. Generally rectangular in shape, apparatus 100 includes a pusher plate 102 which is generally detachable from apparatus 100. Pusher plate 102 includes a plurality of protrusions 104, a medical device retaining member 106, a medical device transfer member 108, a package support member 110 and an optional base 112 which may not be necessary in some embodiments of the present invention. Pusher plate 102 and transfer member 108 are movable in the Y direction relative to base 112, as shown by arrows A1 and A2, respectively, in FIGS. 1A and 1B. Medical device retaining member 106 is movable in the X direction relative to base 112, as shown by arrow A3 in FIGS. 1A and 1B. Package support member 110 is fixedly mounted on base 112 by, for example, welding or at least one screw. Base 112 is depicted in FIGS. 1A and 1B as including a first base member 113 and a second base member 114. One skilled in the art will recognize that base 112 can also be formed as one piece by, for example, machining or molding processes.

Apparatus 100 further includes an optional means for moving pusher plate (e.g., a rod 115 which may be, for example, a telescoping rod permanently mounted on base 112) and an optional shield 116 (which may be, for example, clear plastic that covers retaining member 106) and transfer member 108. Those skilled in the art will recognize that pusher plate 102 can also be moved manually. Apparatus 100 is typically formed of metal and can also be formed of relatively rigid plastic including, for example polycarbonate, polyester, or polystyrene.

Figure 2:
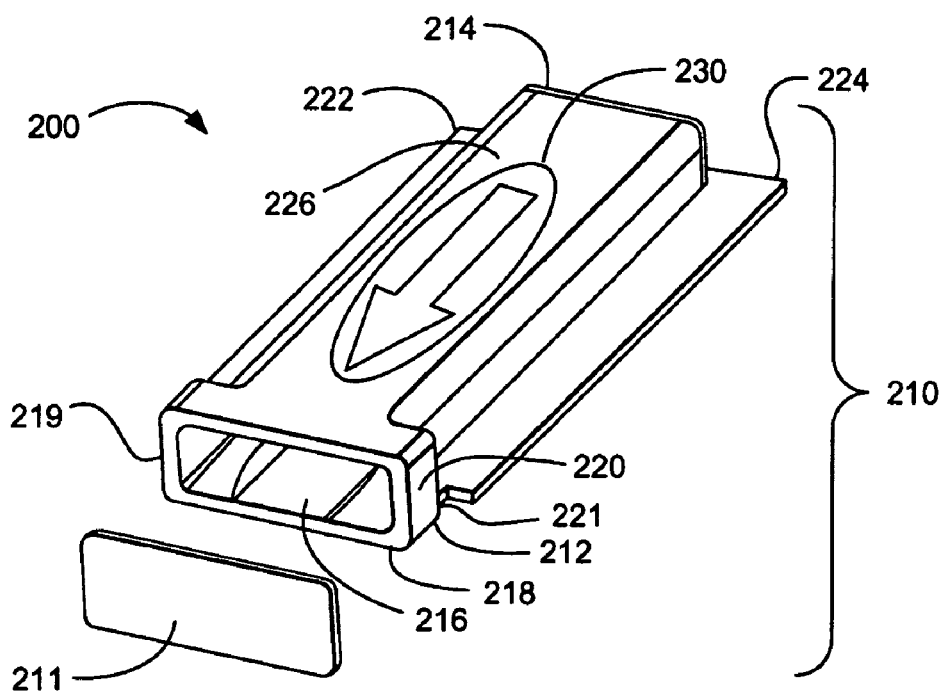
FIG. 2 is a simplified perspective view of a medical device package that can be used with exemplary embodiments of the apparatus according to the present invention.

FIG. 2 is a simplified perspective view of a non-limiting example of a medical device package 200 that can be used in conjunction with apparatus 100 according to one aspect of the present invention. Medical device package 200 includes a main cap member 210 and a minor cap member 211. Main cap member 210 includes a proximal end 212, a distal end 214 and a cavity (not shown) therein. The cavity has an opening 216 at proximal end 212 of main cap member 210 and is configured to receive, and to securely and removably retain, a medical device (e.g., integrated medical device 300, illustrated in FIG. 3) at least partially therein. Opening 216 is bounded by a rim 218 of sufficient surface area to enable minor cap member 211 to be adhered to rim 218 by processes known to those skilled in the art, including, for example heat sealing processes. In this manner, minor cap member 211 and main cap member 210 of medical device package 200 provide a sterility barrier and humidity protection for a medical device contained therein. Rim 218 includes a first outer rim surface 219 and a second outer rim surface 220, either and/or both of which can be engaged by transfer member 108 during use of apparatus 100, as will be described below. Main cap member 210 further includes a first peripheral edge 222, a second peripheral edge 224 and a main cap upper surface 226. First and second peripheral edges 222 and 224 are truncated to end at a distal edge 221 of rim 218. Main cap upper surface 226 optionally includes a directional marker 230 that is discontinuous with (e.g., raised above or, alternatively, recessed below) the remainder of main cap upper surface 226. A plurality of medical device packages 200 can be at least partially attached to each other (i.e., by removably attaching at least a portion of first peripheral edge 222 of one medical device package 200 to at least a portion of second peripheral edge 224 of another package) to form a "chain" of medical device packages 200. Further descriptions of medical device packages 200 that can be used in conjunction with apparatus 100 according to the present invention are in the aforementioned co-pending U.S. patent application Ser. No. 10/666,154.

Figure 3:
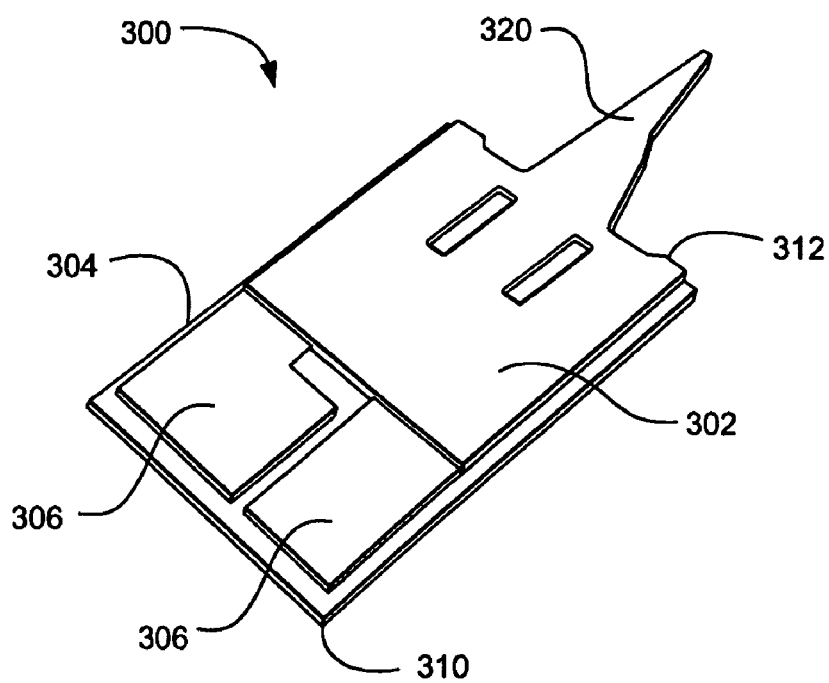
FIG. 3 is a simplified perspective view of a medical device that can be used with exemplary embodiments of the apparatus according to the present invention.

FIG. 3 is a simplified perspective view of an exemplary integrated medical device 300 that can be loaded into medical device package 200 using apparatus 100 according to one aspect of the present invention. Integrated medical device 300 includes a test strip 304 and a dermal tissue penetration member 302. Test strip 304 has a reaction area (not shown) and electrical contacts 306 that terminate on a proximal end 310 of integrated medical device 300. Electrical contacts 306 are made of any suitable conductive material, such as gold, silver, platinum or carbon. Dermal tissue penetration member 302 includes a lancet 320 adapted to pierce a user's skin and draw blood into the reaction area. Further descriptions of integrated medical devices 300 that can be loaded into medical device package 200 using assembly apparatus 100 according to the present invention are in the aforementioned International Application No. PCT/GB01/65634 and U.S. patent application Ser. No. 10/143,399.

Referring again to FIGS. 1A and 1B, medical device retaining member 106 includes a first side 117, a second side 118, a first end 120, a second end 122, an upper surface 124 and a lower surface 126. A plurality of grooves 128 is located on upper surface 124 of medical device retaining member 106 for the plurality of protrusions 104 to move therethrough. The function of protrusions 104 is to move through grooves 128, thereby pushing integrated medical devices 300 retained in grooves 128 onto transfer member 108 during the manufacturing process, as will be described in more detail below (see FIGS. 4 and 5D). Grooves 128 are each bound by at least one wall 130 approximately perpendicular to upper surface 124 (i.e., in the Z direction). Near the top of each wall 130 is at least one ledge 132 for receiving and removably retaining integrated medical device 300 at least partially within the upper region of each groove 128. The width of groove 128 above ledge 132 (i.e., in the X direction) is marginally larger (e.g., about 1–3%) than the width of integrated medical device 300 such that integrated medical device 300 fits snugly therein. The number of grooves 128 can range from 10 to 100 and typically ranges from 20 to 50. Retaining member 106 can move reversibly in the X direction to index by one device width during the device loading process, as will be described below (see FIG. 4).

Medical device transfer member 108 is adjacent to retaining member second side 118 and is intended to shuttle medical devices from retaining member 106 to package support member 110 such that protrusions 104 can then urge the devices into medical device packages 200. Transfer member 108 includes a first side 134, a second side 136, a first end 138, a second end 140, an upper surface 142 and a lower surface 144. A plurality of upper grooves 146 is located on upper surface 142 of transfer member 108, each of which is bound by at least one wall 148 approximately perpendicular to upper surface 142 (i.e., in the Z direction). Near the top of each wall 148 is at least one ledge 150 for receiving and removably retaining integrated medical device 300 at least partially within each upper groove 146. The number of upper grooves 146 typically can range from 5 to 10, although other ranges are possible. The maximum number of upper grooves 146 is dictated by how far away from the center of opening 216 integrated medical device 300 can be delivered. As the number of upper grooves 146 increases, loading accuracy decreases across the plurality of medical device packages 200. The width of upper grooves 146 above ledge 150 (i.e., in the X direction) is marginally larger (e.g., about 1–3%) than the width of integrated medical device 300 such that integrated medical device 300 fits snugly therein. This snug fit minimizes side-to-side movement of the device during the package loading process.

Transfer member 108 further includes at least one protuberance 152 (e.g., a pin) and at least two projections 154 (e.g., lugs) (see FIG. 1B). Protuberance 152 engages with at least one indentation on retaining member second side 118 for receiving protuberance 152 such that grooves 128 and upper grooves 146, are held in alignment during the package loading process. Projections 154 are intended to mate with first outer rim surfaces 219 and second outer rim surface 220 of at least one medical device package 200 or of at least two adjacent medical device packages 200 such that integrated medical device 300 is centered within opening 216 of all packages during the loading process, within the tolerance range required for effective loading (see FIG. 5D).

Grooves 128 and 146 and ledges 132 and 150 can be formed by processes known to those skilled in the art including, but not limited to, spark erosion and electrical discharge machining (EDM). Types of EDM include, for example, wire, sinker and small hole EDM.

Package support member 110 is adjacent to transfer member second side 136.

Support member 110 includes a first side 158, a second side 160, a first end 162, a second end 164, an upper surface 166 and a lower surface 168. A plurality of recesses 170 for supporting a plurality of packages 200 is located on upper surface 166.

Figure 4:
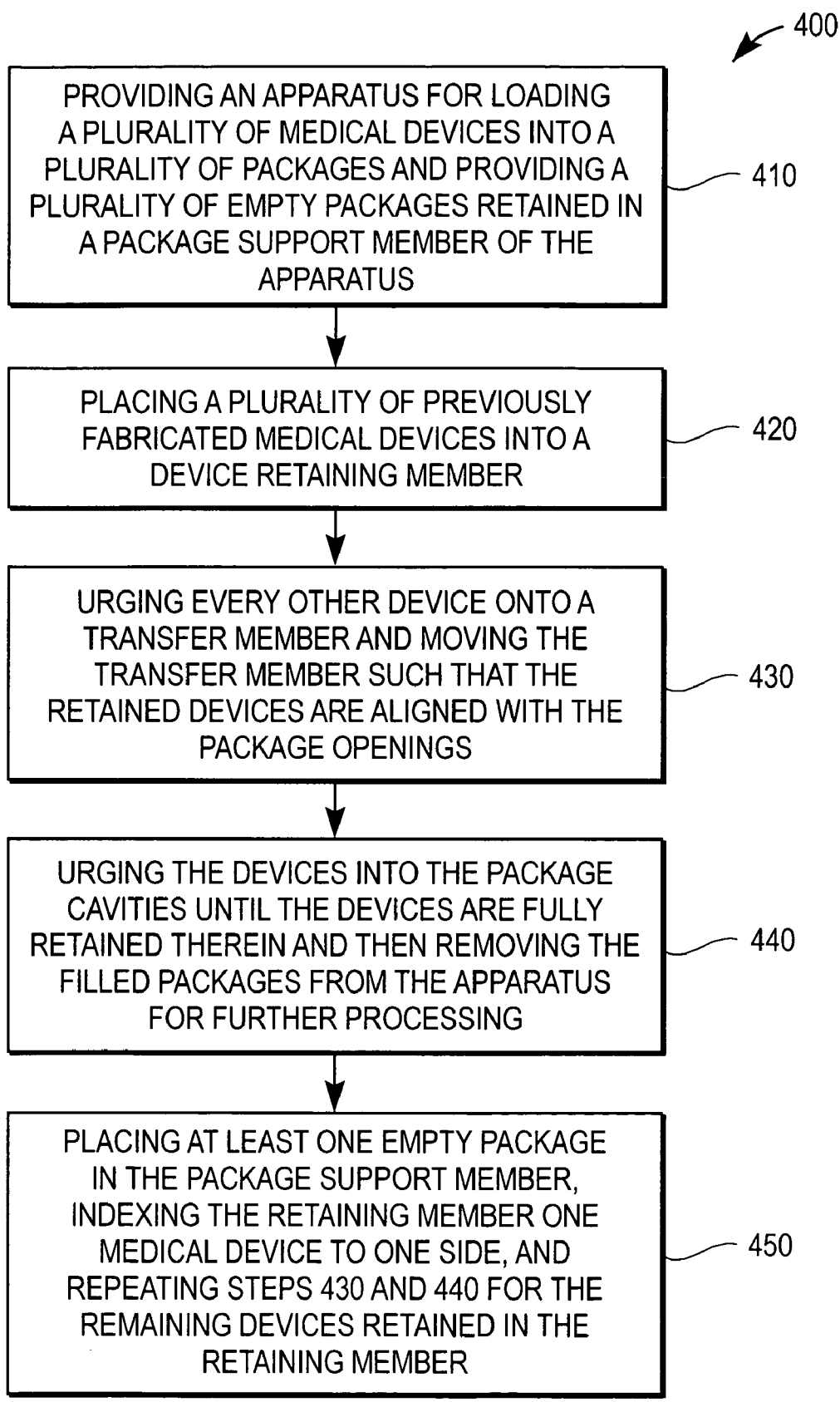
FIG. 4 is a flow chart illustrating an exemplary sequence of steps in a process for loading a plurality of integrated medical devices into a plurality of packages using the loading apparatus according to an exemplary embodiment of the present invention.

FIG. 4 is a flow chart illustrating a sequence of steps in a process 400 for loading a plurality of integrated medical devices (e.g., integrated medical device 300 of FIG. 3) into a plurality of medical device packages (e.g., medical device packages 200 of FIG. 2) according to an exemplary embodiment of the present invention. Process 400 is described below utilizing FIGS. 5A–5F (schematic, perspective views depicting various stages of process 400).

Figure 5A:
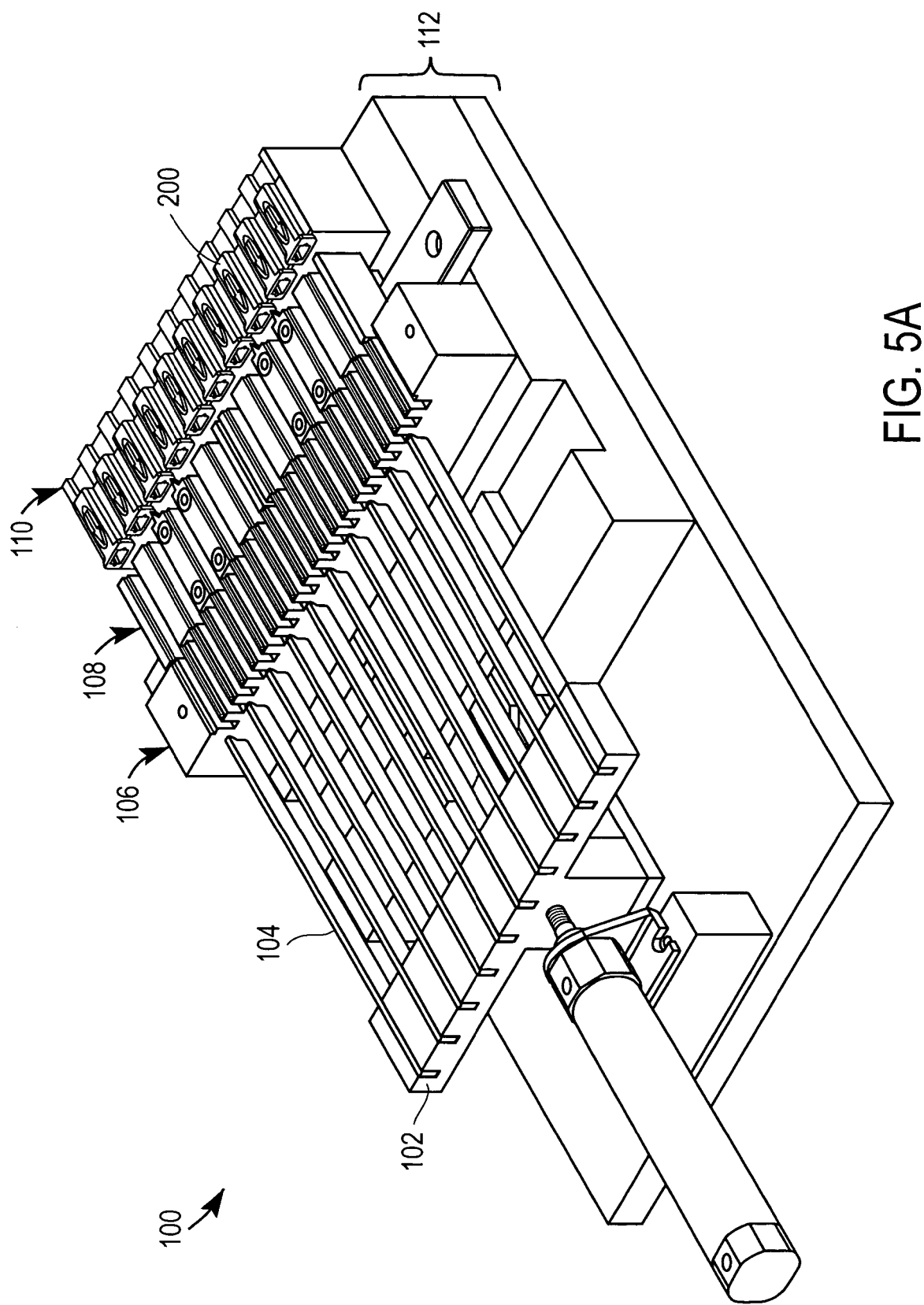
FIGS. 5A–5F are simplified schematic, perspective views depicting various stages of a process for loading medical devices into packages according to an embodiment of the present invention.

Process 400 includes first providing an apparatus 100 according to the present invention and as described above, as set forth in FIG. 4 (see FIG. 5A). The provided apparatus 100 includes a detachable medical device pusher plate 102 with a plurality of protrusions 104, a medical device retaining member 106, a medical device transfer member 108, a package support member 110 and a base 112. Further, a plurality of medical device packages 200 which may be interconnected or unitary is retained in package support member 110.

Figure 5B:
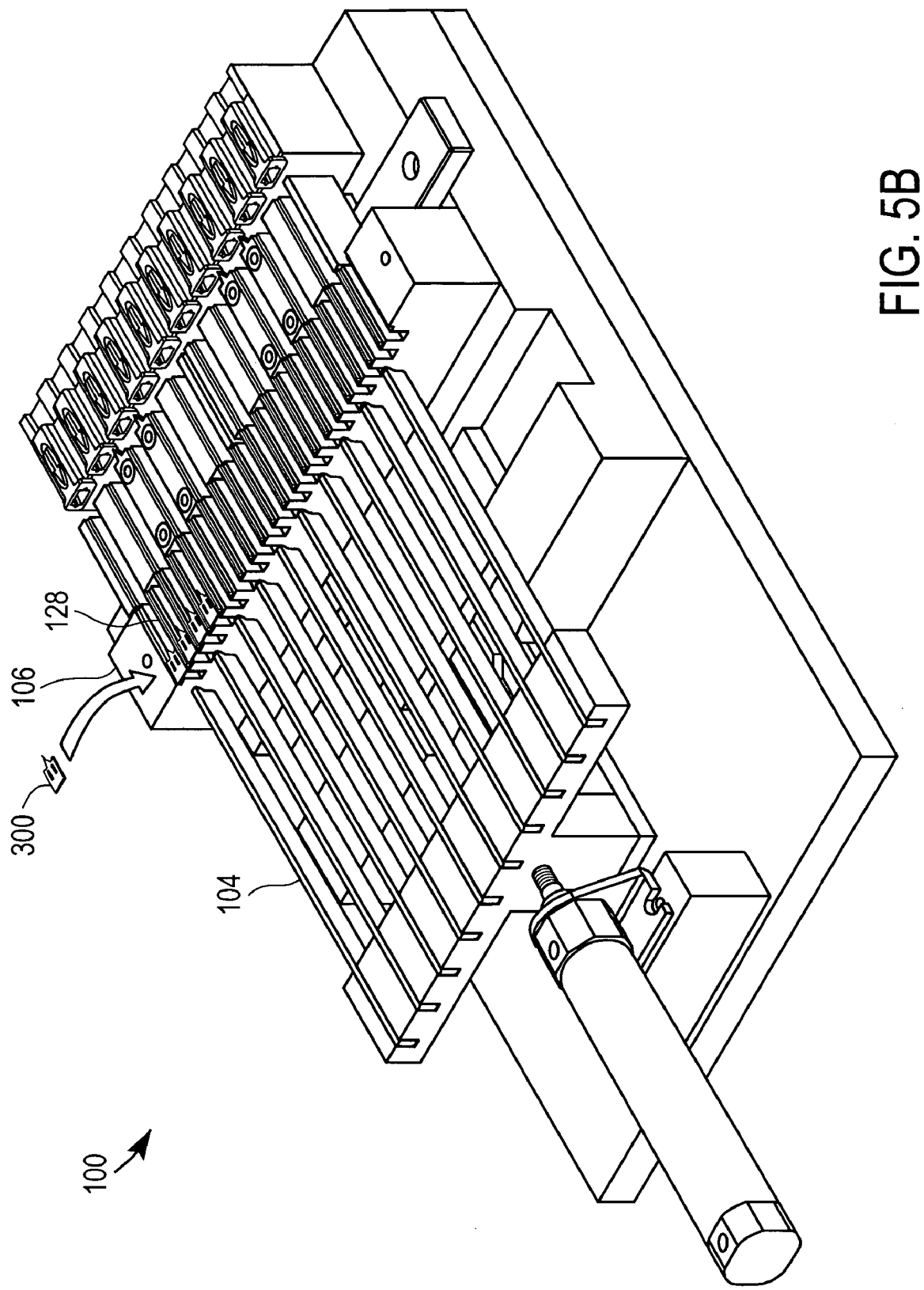
Figure 5C:
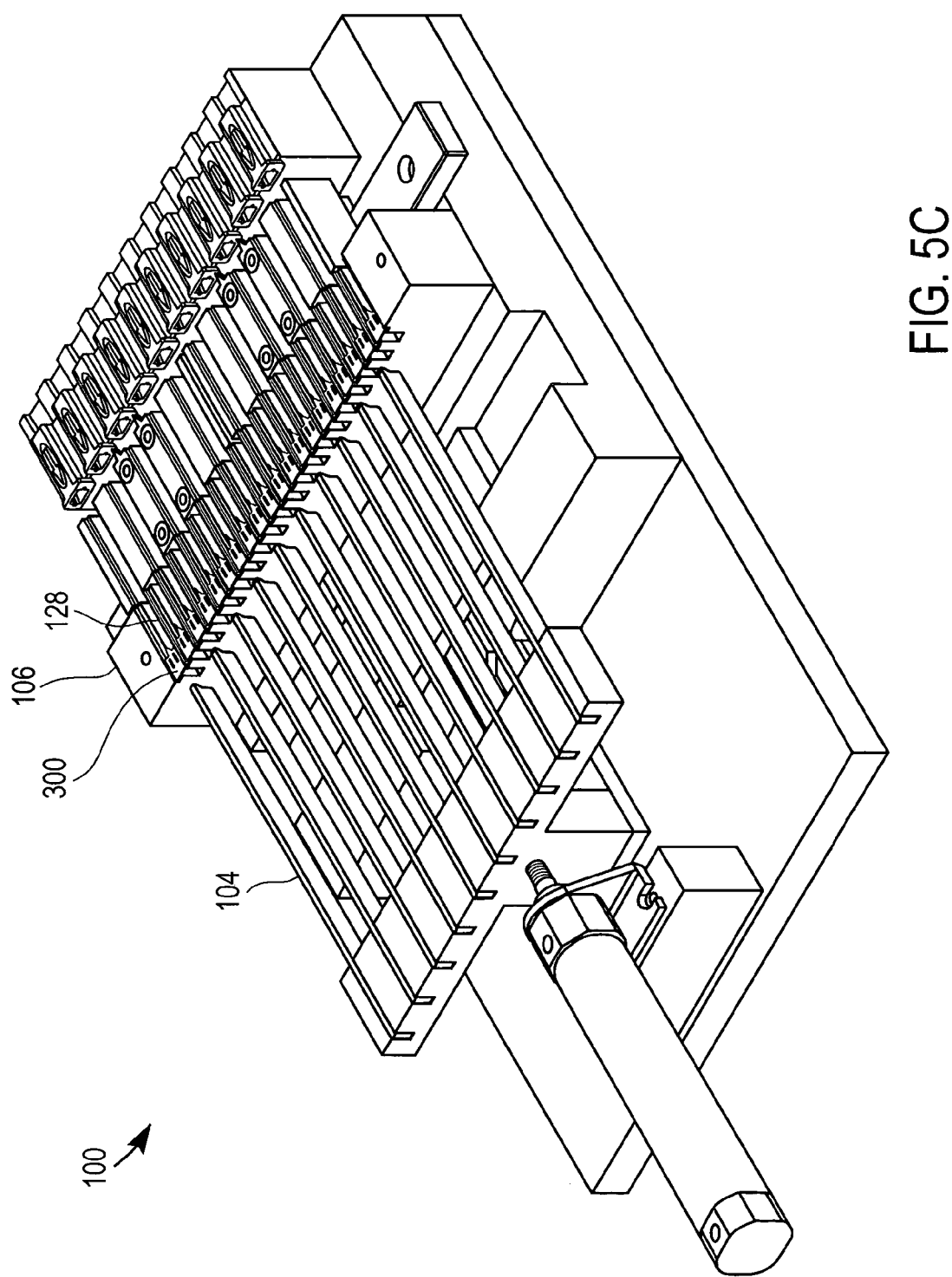

Next, a plurality of previously fabricated integrated medical devices 300 is placed in a plurality of grooves 128 in retaining member 106 (see FIGS. 5B and 5C). Integrated medical devices 300 used in process 400 can be assembled, for example, by a process as described in U.S. patent application Ser. No. 10/881,306 filed Jun. 29, 2004.

Figure 5D:
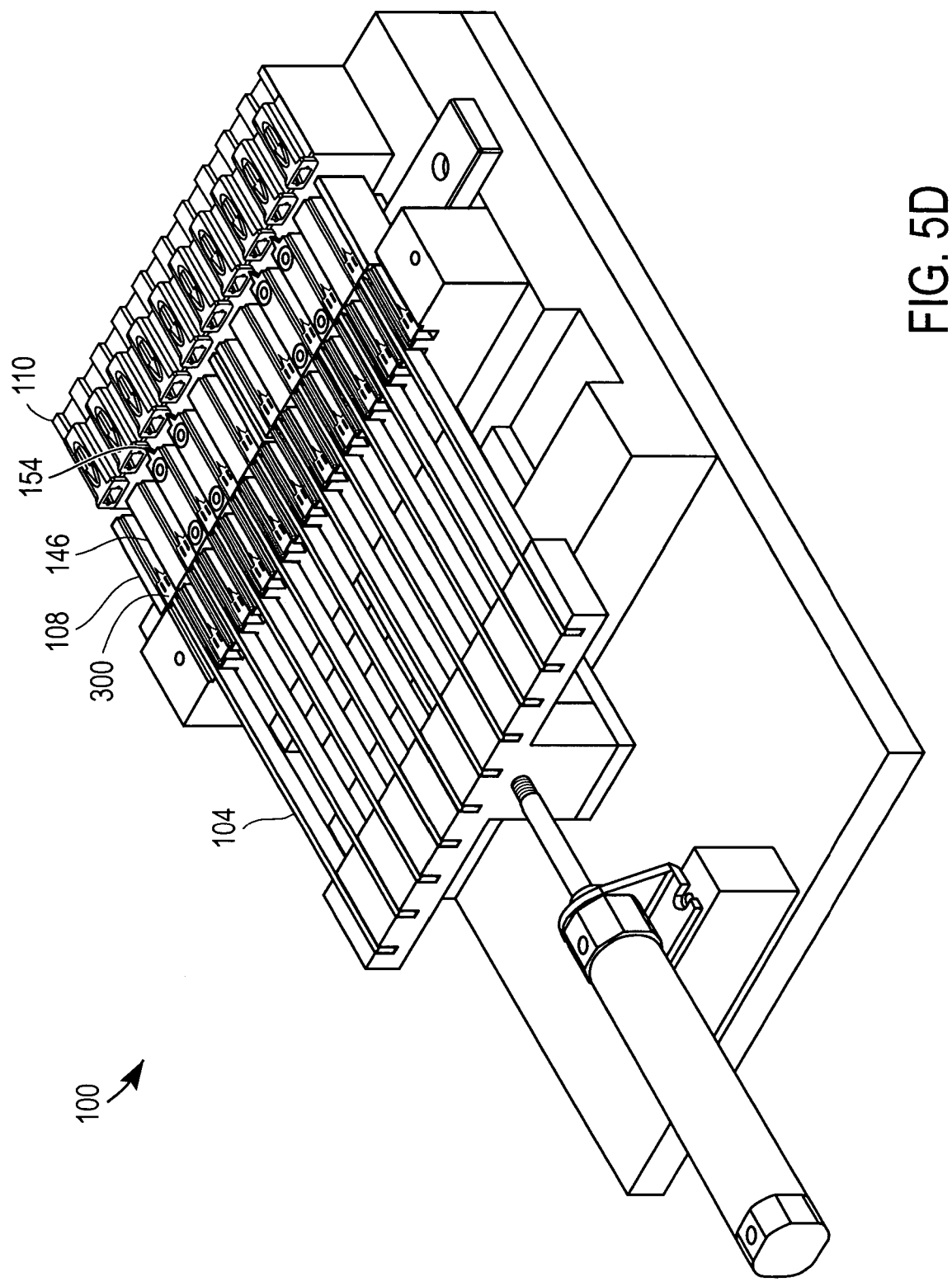
Figure 5E:
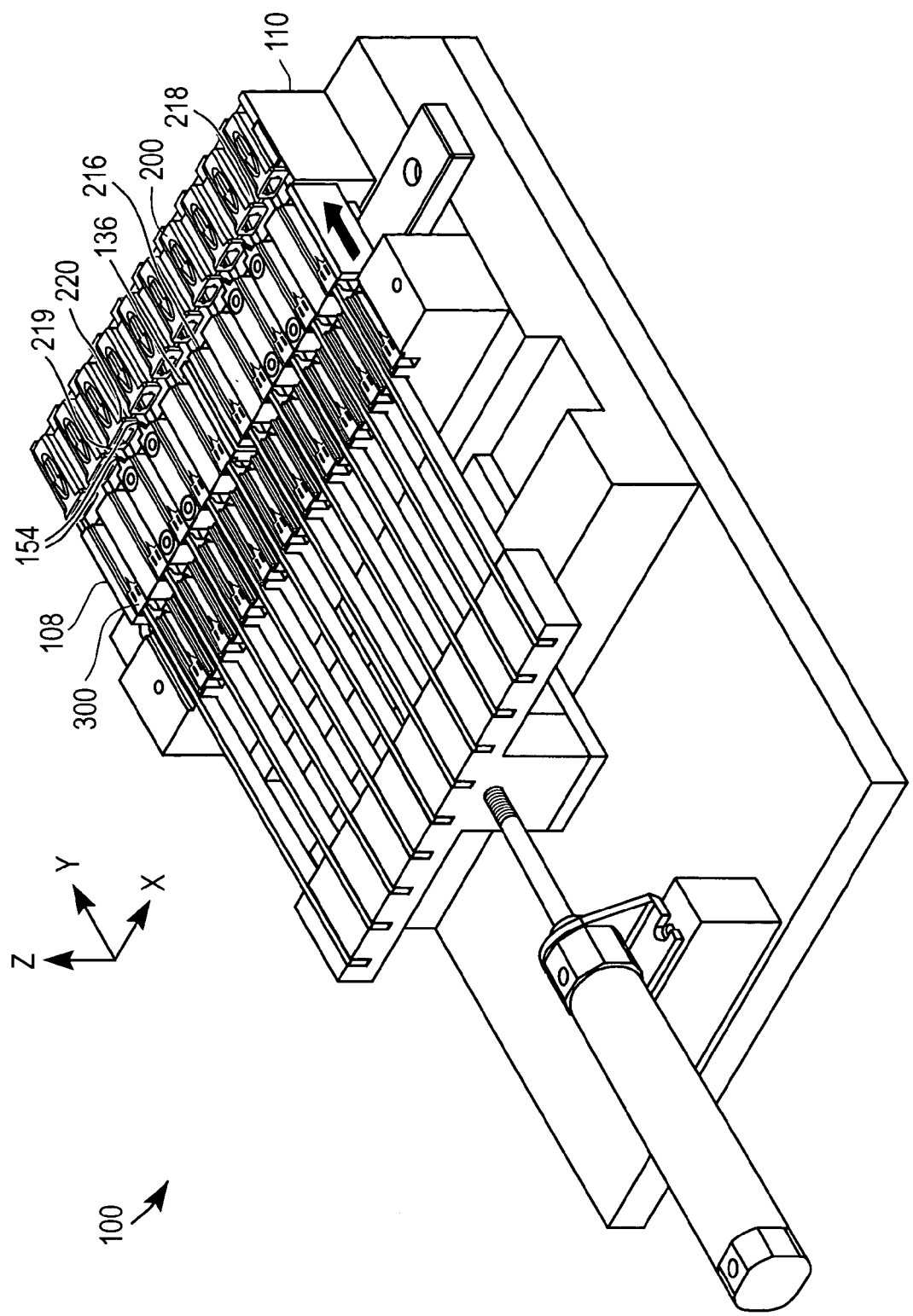

As set forth, upper protrusions 104 next urge every other integrated medical device 300 into a plurality of upper grooves 146 on an upper surface of transfer member 108 (see FIG. 5D). Transfer member 108 is then moved toward package support member 110 until at least two projections 154 on a second side 136 of transfer member 108 engage a first outer rim surface 219 on at least one medical device package 200 and a second outer rim surface 220 on at least another medical device package 200 retained in support member such that integrated medical devices 300 are centered in an opening 216 in each medical device package 200 within the required tolerances (see FIG. 5E). The at least two projections 154 can also engage first and second outer rim surfaces 219 and 220 on the at least one medical device package 200. Centering integrated medical devices 300 in at least one opening 216 beneficially accommodates variations in the dimension in the X direction such that the plurality of integrated medical devices 300 are accurately loaded into each of the plurality of medical device packages 200.

Figure 5F:
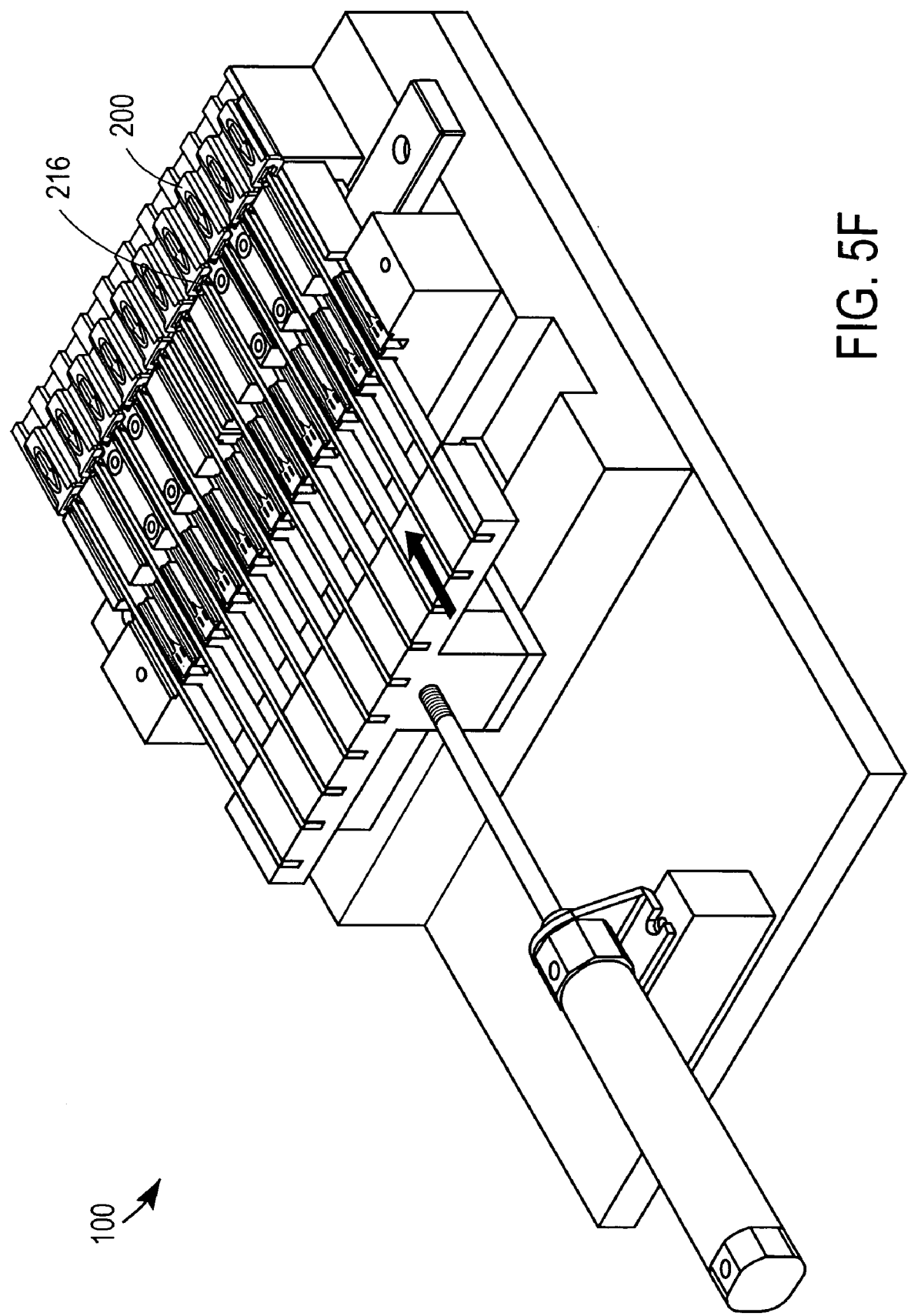

Next, each integrated medical device 300 is urged into the opening 216 of each medical device package 200 until each medical device package 200 is inserted into the package cavity and is fully retained therein, as set forth (see FIG. 5F). The packages containing medical devices are then removed for further processing.

As set forth, the protrusions 104 of pusher plate 102 are retracted, a plurality of empty packages is placed in recesses 110, and the device retainer member is indexed one device in the X direction (e.g., to the left). The remaining devices are then loaded into the plurality of packages by repeating the steps above.

Including twice the number of grooves in retaining member 106 relative to transfer member 108 and package support member 110 beneficially increases process efficiency because loading twenty integrated medical devices 300 into retaining member 106 and then transferring ten integrated medical devices 300, for example, at a time twice from retaining member 106 is faster than loading ten integrated medical devices 300 into retaining member 106 at the start of each loading sequence.

Each of the steps of process 400 can be performed, for example, either manually by a user or with the aid of a mechanical and/or electrical device.

Once apprised of the present disclosure, one skilled in the art will recognize that a variety of medical devices can be used in the present invention. Such medical devices include, but are not limited to, integrated medical devices that include a combination of a test strip and a lancet, examples of which are described in the aforementioned International Application No. PCT/GB01/05634 (published as WO 02/49507 on Jun. 27, 2002) and U.S. patent application Ser. No. 10/143,399, both of which are fully incorporated herein by reference. One skilled in the art will also recognize that such test strips may have, but are not limited to, an electrochemical or photometric configuration. For illustrative purposes only, medical devices in various figures of the present disclosure were depicted as having an electrochemical configuration.

Moreover, those skilled in the art will appreciate that medical devices according to embodiments of the present invention can be adapted for the measurement of, for example, glucose, ketones, glycated albumin, coagulation parameters and cholesterol of a sample.

In addition, one skilled in the art will recognize that medical devices according to the present invention may be contained within a combined sample collection and metering system designed for in-situ testing. Examples of such systems designed for in-situ testing are disclosed in International Patent Application No. PCT/US01/07169 (published as WO 01/64105 A1 on Sep. 7, 2001) and International Patent Application No. PCT/GB02/03772 (published as WO 03/015627 A1 on Feb. 27, 2003), each of which is fully incorporated herein by reference.

It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of loading a plurality of medical devices into a plurality of medical device packages, said method comprising:
   providing an apparatus including:
      a pusher plate;
      a medical device retaining member;
      a transfer member; and
      a package support member,
      wherein said device retaining member and said transfer member include a plurality of grooves for receiving and removably retaining a plurality of medical devices and
      wherein said package support member includes a plurality of recesses for receiving and removably retaining said plurality of medical device packages therein;
   loading a plurality of packages into said package support member recesses;
   loading a plurality of integrated medical devices into the retaining member grooves;
   transferring half of said plurality of integrated medical devices from said retaining member to said transfer member by pushing with said pusher plate every other medical device in the grooves of the retaining member into the respective grooves of the transfer member;
   urging the transfer member into alignment with said package support member;
   inserting said plurality of integrated medical devices in said transfer member into said plurality of packages in said support member by further pushing said pusher plate; and
   removing said packages from said apparatus for further processing.

* * * * *